United States Patent [19]
Yasuda

[11] Patent Number: 5,910,591
[45] Date of Patent: Jun. 8, 1999

[54] METHOD OF PREPARATION OF 4-HYDROXY-1,2,2,6,6-PENTAMETHYLPIPERIDINE

[75] Inventor: Masaaki Yasuda, Kuga-gun, Japan

[73] Assignee: Mitsui Chemicals, Inc., Tokyo, Japan

[21] Appl. No.: 08/953,517

[22] Filed: Oct. 17, 1997

[30] Foreign Application Priority Data

Oct. 17, 1996 [JP] Japan ................................. 8-274753
Nov. 21, 1996 [JP] Japan ................................. 8-310386

[51] Int. Cl.⁶ ................................................. C07D 211/44
[52] U.S. Cl. ............................................................. 546/242
[58] Field of Search .............................................. 546/242

[56] References Cited

U.S. PATENT DOCUMENTS

| | | | |
|---|---|---|---|
| 3,364,220 | 1/1968 | Biel et al. | 260/293 |
| 3,974,127 | 8/1976 | Tanikella et al. | 260/75 |
| 5,840,905 | 11/1998 | Nitsche et al. | 546/184 |

FOREIGN PATENT DOCUMENTS

| | | |
|---|---|---|
| 0225850 | 6/1987 | European Pat. Off. . |
| 0375612 | 6/1990 | European Pat. Off. . |
| 2-212479 | 8/1990 | Japan . |

OTHER PUBLICATIONS

Zhelyazkov et al., "Synthesis of some substituted 2,2,6,6–tetramethylpiperidines," Chemical Abstract, vol. 60, No. 3, p. 2881, Feb. 3, 1964.

Bates et al., "Isolation Techniques" in Research Techniques in Organic Chemistry, Prentic–Hall Inc., pp. 42–63, 1971.
Chemical Abstracts, vol. 126, No. 21, 277401w (May 26, 1997), Konopikova et al.
Chemical Abstracts, vol. 124, No. 20, 274220j (May 13, 1996), Wang.

*Primary Examiner*—Mukund J. Shah
*Assistant Examiner*—Ann M. Kessinger
*Attorney, Agent, or Firm*—Sherman and Shalloway

[57] ABSTRACT

The present invention relates to a method for preparing 4-hydroxy-1,2,2,6,6-pentamethylpiperidine comprising the following steps:

(i) reacting 4-hydroxy-2,2,6,6-tetramethylpiperidine with at least one compound selected from the group consisting of formaldehyde, paraformaldehyde and trioxane, optionally in the presence of formic acid;

(ii) neutralizing the reaction product of step (i) by adding a base thereto; and (iii) after the neutralization, separating the crude product from the aqueous layer and crystallizing and filtering the crude product to thereby obtain crystals of 4-hydroxy-1,2,2,6,6-pentamethylpiperidine with a water content of 3% by weight or less. The present invention also relates to a method for preparing 4-hydroxy-1,2,2,6,6-pentamethylpiperidine, comprising reacting 4-hydroxy-2,2,6,6-tetramethylpiperidine with at least one compound selected from the group consisting of formaldehyde, paraformaldehyde and trioxane, optionally in the presence of formic acid added in an amount smaller than that of 4-hydroxy-2,2,6,6-tetramethylpiperidine in terms of mole.

9 Claims, No Drawings

METHOD OF PREPARATION OF 4-HYDROXY-1,2,2,6,6-PENTAMETHYLPIPERIDINE

BACKGROUND OF THE INVENTION

The present invention relates to a method for preparing 4-hydroxy-1,2,2,6,6-pentamethylpiperidine (hereinafter, sometimes abbreviated to "N-methyl-TAAM") through methylation of 4-hydroxy-2,2,6,6-tetramethylpiperidine (known as triacetonalkamine; hereinafter, sometimes abbreviated to "TAAM").

N-methyl-TAAM is useful as a starting material for synthesizing sterically hindered piperidine compounds used as photostabilizers for plastics.

N-methyl-TAAM is prepared through methylation of TAAM, for example, by N-methylation of TAAM using formaldehyde/formic acid, which is known as the Eschweiler-Clarke reaction. This reaction is believed to proceed by the mechanism described below, with the formic acid being considered to play the role of reducing the enamine intermediate.

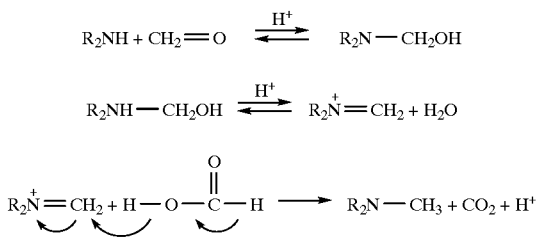

As references concerning this reaction, U.S. Pat. No. 3,974,127 and Japanese Unexamined Patent Publication No. 2-212479 are given.

U.S. Pat. No. 3,974,127 teaches that N-methylation of TAAM is performed by adding 18 g of 37% aqueous formaldehyde and 4 ml of formic acid containing 1% of water to 18 g of TAAM; thereafter, sodium hydroxide is added to the reaction mixture; and the reaction product is extracted with an ether.

Japanese Unexamined Patent Publication No. 2-212479 teaches that formaldehyde or paraformaldehyde which are at least 20 mole % in excess over TAAM and a substantially stoichiometric amount of formic acid are reacted and that a base is added to the reaction mixture before distillation of the reaction product.

SUMMARY OF THE INVENTION

According to the investigation performed by the present inventors, it has been found that when TAAM, formaldehyde or paraformaldehyde, and, optionally, formic acid are reacted to prepare N-methyl-TAAM, the reaction product contains not only N-methyl-TAAM which is the product of interest but also impurities such as formaldehyde, formic acid, etc. and water.

Part of the formic acid is present in the form of a formate of N-methyl-TAAM. This formate is highly miscible with organic solvents and difficult to isolate/purify by crystallization.

It is desirable to neutralize and remove these impurities before isolation/purification of the product of interest in order to improve its purity and yield.

Neutralization is performed by adding a base to the reaction product described above.

According to the finding of the present inventors, the crude product separated from the aqueous layer after neutralization contains a monohydrated salt of N-methyl-TAAM. The monohydrated salt of N-methyl-TAAM has a melting point of approximately 50° C., which is lower than the melting point of N-methyl-TAAM by as much as 20° C. Thus, drying must be performed after purification at low temperature over a long period of time.

From an industrial point of view, the expenses for treating the effluent from the neutralization step as a factor that raises the production cost of N-methyl-TAAM.

U.S. Pat. No. 3,364,220 supra does not describe anything about the base concentration of the reaction system in the neutralization step, the reduction of the effluent from the neutralization step, and the reduction of water content of crystals.

In Japanese Unexamined Patent Publication No. 2-212479, 50% aqueous NaOH is added to the reaction mixture before it is worked up. However, NaOH is diluted by the water already present in the system, and the NaOH concentration in the aqueous layer after neutralization is not mentioned. This reference describes nothing about reduction of the effluent nor reduction of the water content of crystals.

Under the circumstances, the present inventors made further researches toward the goal of shortening the time for drying N-methyl-TAAM and reducing the effluent from the neutralization step. As a result, it has been found that, surprisingly enough, the above objects can be attained by increasing the base concentration in the aqueous layer that is obtained after neutralization.

The present invention provides a method for preparing 4-hydroxy-1,2,2,6,6-pentamethylpiperidine comprising the following steps:

(i) reacting 4-hydroxy-2,2,6,6-tetramethylpiperidine with at least one compound selected from the group consisting of formaldehyde, paraformaldehyde and trioxane, optionally in the presence of added formic acid;

(ii) neutralizing the reaction product of step (i) by adding a base thereto; and (iii) after the neutralization, separating the crude product from the aqueous layer and crystallizing and filtering the crude product to thereby obtain crystals of 4-hydroxy-1,2,2,6,6-pentamethylpiperidine with a water content of 3% by weight or less.

According to the present invention, the water content of the end product N-methyl-TAAM can be reduced. Also, the aqueous layer that is obtained after neutralization can be used repeatedly, enabling reduction of the effluent.

On the other hand, formic acid is a highly corrosive substance that is difficult to handle from a safety viewpoint. It is necessary to make the formic acid feeding equipment corrosion resistant, and this is a factor that increases the production cost of N-methyl-TAAM.

Under the circumstances, the present inventors reduced the amount of use of formic acid and found, surprisingly that the end product N-methyl-TAAM could be obtained at high yield. This finding has led to the accomplishment of the present invention.

According to the reaction mechanism described above, it is supposed that using formic acid in an amount at least equal to that of TAAM in terms of mole is necessary. Unexpectedly, however, N-methyl-TAAM can be obtained at high yields comparable to those achieved in conventional methods even if formic acid is used in smaller amounts than has been conventionally considered necessary or even if it is not used at all.

The present invention provides a method for preparing 4-hydroxy-1,2,2,6,6-pentamethylpiperidine, comprising reacting 4-hydroxy-2,2,6,6-tetramethylpiperidine with at least one compound selected from the group consisting of formaldehyde, paraformaldehyde and trioxane, optionally in the presence of formic acid added in an amount smaller in terms of mole than that of 4-hydroxy-2,2,6,6-tetramethylpiperidine.

It has been considered essential to use at least an equivalent amount of formic acid in the reaction for synthesizing N-methyl-TAAM by N-methylating TAAM with formaldehyde. However, according to the present invention, N-Me-TAAM can be obtained at high yield with selectivity comparable to those achieved in conventional methods even if formic acid is not used.

DETAILED DESCRIPTION OF THE INVENTION

The individual steps of the method of the invention for preparing 4-hydroxy-1,2,2,6,6-pentamethylpiperidine will be described below.

(i) Methylation Step

TAAM used as the starting material is prepared by, for example, hydrogenating 4-oxo-2,2,6,6-tetramethylpiperidine in water as a solvent in the presence of a catalyst such as Raney nickel or ruthenium. In the present invention, the solution resulting from hydrogenation may be used either as it is or after concentration or isolation/purification.

The methylation of TAAM will now be described.

Formaldehyde, paraformaldehyde and trioxane may be used independently or in combination. The amount of addition of at least one compound selected from the group consisting of formaldehyde, paraformaldehyde and trioxane (as calculated for formaldehyde) is usually 1 to 4 times, preferably 1.5 to 3.0 times, the amount of TAAM in terms of mole. Use of the above-mentioned compounds within the preferred range will lead to a higher yield of the end product and reduce the amount of a base used in the subsequent neutralization step.

At least one compound selected from the group consisting of formaldehyde, paraformaldehyde and trioxane may be added to TAAM all at a time when the reaction starts, or part of the compound may first be mixed with TAAM and melted by heating and the remainder may subsequently be fed to the reaction mixture.

Preferably, formaldehyde is used as a 35–37% aqueous solution.

The amount of addition of formic acid is usually 0 to 3, preferably 0 to 1, more preferably less than 1, and more preferably 0 to 0.5, times the amount of TAAM in terms of mole. The amount of addition 0 (zero) means an embodiment in which formic acid is not added. This embodiment is the most preferable in the present invention.

When formic acid is to be added, all of it may be added to TAAM at the initiation of the reaction, or part of it may first be mixed with at least one compound selected from the group consisting of formaldehyde, paraformaldehyde and trioxane and melted or dissolved by heating and the remainder may subsequently be fed to the reaction mixture.

The reaction temperature is usually 60–160° C., preferably 90–160° C.

The reaction time is usually 1–10 hr, preferably 1–2 hr.

A solvent may be used in this reaction. Specific examples of the solvent include water and methanol. Preferably, water is used.

Raising the temperature of the reaction mixture to 120–160° C., preferably 130–160° C. before completion of the reaction, is preferable since water, the unreacted formaldehyde and formic acid, by-products such as carbon dioxide, etc. are removed from the reaction mixture to produce N-methyl-TAAM in a concentrated form. The reaction is usually performed under atmospheric pressure.

Especially preferred reaction conditions may be exemplified by the following. First, TAAM is mixed with at least one compound selected from the group consisting of formaldehyde, paraformaldehyde and trioxane in an amount (as calculated for formaldehyde) ranging from one half to an amount equal to that of TAAM in terms of mole, and the mixture is melted or dissolved by heating. Then, while agitating the mixture, at least one compound selected from the group consisting of formaldehyde, paraformaldehyde and trioxane is additionally fed to the mixture in an amount (as calculated for formaldehyde) of 1.0 to 2.0 times the amount of TAAM in terms of mole, and the reaction mixture is heated to 95–100° C. and reacted for 0.5–2 hr. Thereafter, the resultant reaction mixture is raised to ca. 140–160° C. to concentrate the N-methyl-TAAM in the reaction mixture.

The water content of the concentrated reaction mixture is preferably 5% by weight or less.

(i-1) Extraction Step

The reaction product which may be concentrated is extracted with a water-immiscible organic solvent before neutralization to thereby transfer the N-methyl-TAAM into the organic solvent layer. Thus, the yield of the end product can be improved.

Specific examples of the organic solvent include aromatic hydrocarbon solvents such as benzene, toluene, xylene; aliphatic or alicyclic hydrocarbons such as n-hexane, n-heptane, cyclohexane, cycloheptane; and ethers.

Alternatively, the mother liquor resulting from the crystallization conducted in step (iii) to be described later may be used as the organic solvent.

The amount of use of the organic solvent is usually 1 to 3 times, preferably 1 to 1.5 times, the weight of the reaction product.

(ii) Neutralization Step

Neutralization is performed by adding a base to the reaction product which has optionally undergone, concentration and/or extraction. In this case, the base concentration in the aqueous layer which is obtained after the neutralization is controlled such that the water content of the crystals of 4-hydroxy-1,2,2,6,6-pentamethylpiperidine is 3% by weight or less. A base is added such that the base concentration in the aqueous layer which is obtained after the neutralization is usually 25% by weight or more, preferably 25–50% by weight or more, more preferably 27–50% by weight.

If the base concentration in the aqueous layer after the neutralization is thus raised, the proportion of the monohydrated salt of N-methyl-TAAM in the end product will be sufficiently reduced to shorten the time for drying crystals.

The base is added as an aqueous solution with a concentration of usually 30–50% by weight, preferably 35–50% by weight. The base thus supplied is diluted by the water contained in the reaction product. However, if the concentration operation described above has been performed in advance to reduce the water content, the base concentration can be maintained high.

As a result, the aqueous layer from which the crude product has been separated after neutralization can be recycled to the neutralization step. This leads to the reduction of the effluent.

As the base, sodium hydroxide, potassium hydroxide, etc. may be enumerated.

The amount of use of the base is usually 0.1 to 1.5, preferably 0.2 to 1.0, times the amount of N-methyl-TAAM in terms of mole.

(iii) Separation/Crystallization Step

After neutralization, the crude product is separated from the aqueous layer and N-methyl-TAAM is isolated and purified from the crude product by crystallization. The aqueous layer from which the crude product has been separated may be recycled to the neutralization step.

As a crystallization solvent, aromatic hydrocarbon solvents such as benzene, toluene, xylene; aliphatic or alicyclic hydrocarbons such as n-hexane, n-heptane, cyclohexane, cycloheptane; and ethers may be used. Especially preferred are aliphatic or alicyclic hydrocarbons.

After crystallization, crystals of N-methyl-TAAM (hereinafter, sometimes referred to the "wet cake") are obtained through filtration. The water content of the wet cake is usually 3% or less, preferably 2% or less by weight.

The wet cake is dried by conventional methods. Since the wet cake obtained by the method of the invention is low in water content, drying can be performed easily.

If desired, the mother liquor resulting from the crystallyzation may be recycled as the extraction solvent in step (i-1) described above.

The present invention also provides another method for preparing 4-hydroxy-1,2,2,6,6-pentamethylpiperidine. According to this alternative method, 4-hydroxy-2,2,6,6-tetramethylpiperidine and at least one compound selected from the group consisting of formaldehyde, paraformaldehyde and trioxane are subjected to methylation, optionally in the presence of formic acid added in an amount smaller than that of 4-hydroxy-2,2,6,6-tetramethylpiperidine in terms of mole; thereafter, the reaction product or concentrated reaction product (hereinafter referred to as the "crude product") may be distilled or crystallized to isolate/purify the desired N-methyl-TAAM. Each step of this procedure is the same as described above.

Prior to the operations of distillation, crystallization, etc., an organic solvent substantially immiscible with water may be added to the crude product to thereby transfer the N-methyl-TAAM to the organic solvent phase. As such an organic solvent, aromatic hydrocarbon solvents such as benzene, toluene, xylene; aliphatic or alicyclic hydrocarbons such as n-hexane, n-heptane, cyclohexane, cycloheptane; and ethers may be enumerated.

A base is added to the crude product (preferably after being transferred to the organic solvent phase) to thereby neutralize excessive formaldehyde and formic acid (including formates of N-methyl-TAAM produced by the reaction). Then, the aqueous layer is separated and removed. Preferably, distillation or crystallization is performed thereafter. After the neutralization, the aqueous layer may be recycled to the neutralization step again. As the base, sodium hydroxide, potassium hydroxide, ammonia, etc. may be enumerated.

Distillation is performed, for example, under a pressure ranging from one atmosphere to 2.7 kPa at a temperature of 100–150° C.

As a crystallization solvent, aromatic hydrocarbon solvents such as benzene, toluene, xylene; aliphatic or alicyclic hydrocarbons such as n-hexane, n-heptane, cyclohexane, cycloheptane; and ethers may be used.

After crystallization, crystals of the desired N-methyl-TAAM are obtained through filtration and drying. The mother liquor resulting from the crystallyzation may be recycled and added to the crude product.

Now, the present invention will be described more specifically below with reference to the following Examples, which should not be construed as limiting the scope of the present invention.

EXAMPLE 1

(1) TAAM containing 10% of water (TAAM: 1.0 mol) and 37% aqueous formaldehyde (HCHO: 1.0 mol) were placed in a reactor provided with a packed column (10×1 cmφ) and the mixture was melted by heating at 70° C. After the temperature was raised to 98° C. (reflux temperature), 37% aqueous formaldehyde (HCHO 1.0 mol) was fed over 1 hr and the reaction was carried out for another 1 hr under atmospheric pressure. Subsequently, the reaction mixture was heated to 140° C. over 2 hr and concentrated.

The reaction yield was 99 mole % or more. The concentrations of individual components in the concentrated solution and the distillate water are shown in Table 1.

TABLE 1

|  | Concentrated solution | Distillate water |
| --- | --- | --- |
| N-methyl-TAAM | 94.8 | 1.15 |
| HCHO | <0.1 | 10.4 |
| TAAM | <0.1 | 0.03 |
| $H_2O$ | 2.55 | — |

(2) The concentrated solution obtained in (1) above was left and cooled to 60° C. Then, Mitsui hexane (Mitsui Petrochemical Industries, Ltd.; boiling point: 68° C.) 1.5 folds by weight of the concentrated solution was added to extract N-methyl-TAAM into the oil layer. Thereafter, 48% by weight aqueous sodium hydroxide solution was added such that the molar ratio of NaOH/N-methyl-TAAM was 0.2, 0.5 and 1.0.

After leaving for a while, the oil layer and the aqueous layer were separated. When the oil layer was gradually cooled to 5° C., crystals began to form at around 21° C. The crystals were rinsed with Mitsui hexane several times and then filtered.

The water content of the wet cake and the NaOH concentration in the aqueous layer obtained after neutralization were as shown in Table 2.

[Method for Determining the Water Content of the Wet Cake]

The water content in about 0.3 g of the crystals obtained after filtration was measured in accordance with JIS-K-0068 using a Karl Fischer moisture content analyzer (Kyoto Electronics Industries, Model MKC-210).

TABLE 2

| NaOH/N-methyl-TAAM (molar ratio) | Water Content of Wet Cake (% by weight) | NaOH Concentration in Aqueous Layer after Neutralization (% by weight) |
| --- | --- | --- |
| 0.2 | 1.8 | 28.8 |
| 0.5 | 1.5 | 32.8 |
| 1.0 | 1.7 | 37.6 |

EXAMPLE 2

Operations were performed in the same manner as in Example 1 except that the molar ratio of NaOH/N-methyl-TAAM was 0.5 and that the concentration of the NaOH to be added was changed.

The resultant wet cake was dried at 60° C. under a pressure of 1.4 kPa for 2 hr.

The results are shown in Table 3.

TABLE 3

| NaOH Concentration (% by weight) | Water Content of Wet Cake (% by weight) | Water Content after Drying (% by weight) | NaOH Concentration in Aqueous Layer after Neutralization (% by weight) |
| --- | --- | --- | --- |
| 10 | 5.8 | 1.8 | 8.9 |
| 20 | 4.8 |  | 17.1 |
| 35 | 1.9 | 0.5 ↓ | 27.6 |
| 48 | 1.6 | 0.5 ↓ | 32.8 |

EXAMPLE 3

Operations were performed in the same manner as in Example 1 except that the molar ratio of NaOH/N-methyl-TAAM was 0.5; that the concentration of the NaOH to be added was 48% by weight; and that the aqueous layer obtained after neutralization was recycled to the neutralization step.

The results are shown in Table 4.

TABLE 4

| No. of Recycles | Water Content of Wet Cake (% by weight) | N-methyl-TAAM Recovery by Crystallization (%) |
| --- | --- | --- |
| 1 | 2.0 | 85 |
| 2 | 2.3 | 84 |

EXAMPLE 4

Operations were performed in the same manner as in Example 1 except the molar ratio of NaOH/N-methyl-TAAM was 0.5; that the concentration of the NaOH to be added was 48% by weight; and that the mother liquor resulting from crystallization was recycled to the extraction step twice. The resultant wet cake was dried at 60° C. under a pressure of 1.4 kPa for 2 hr. The yield of N-methyl-TAAM after drying was 98% and its water content was 0.5% by weight or less.

EXAMPLE 5

Eighty percent aqueous TAAM solution and 37% aqueous formaldehyde were placed in a reactor. The mixture was heated to 100° C. and reacted under the conditions described in Table 5 below. The results are shown in Table 5.

TABLE 5

| HCHO/TAAM (molar ratio) | Reaction Time (hr) | TAAM Conversion (mole %) | Yield of N-methyl-TAAM (mole %) | Selectivity for N-methyl-TAAM (mole %) |
| --- | --- | --- | --- | --- |
| 2.2 | 4 | 97.5 | 94.0 | 96.2 |
| " | 6 | 99.5 | 97.5 | 98.2 |
| 2.6 | 4 | 99.5 | 98.0 | 98.5 |
| " | 6 | 99.9 | 99.0 | 99.1 |
| 3.0 | 4 | 99.9 | 99.0 | 99.1 |

EXAMPLE 6

Eighty percent aqueous TAAM solution and 37% aqueous formaldehyde were placed in a reactor provided with a packed column (10×1 cmφ). The mixture was dissolved by heating at 90° C. Then, the mixture was heated to 98° C. (reflux temperature) and reacted under atmospheric pressure for 1 hr. Thereafter, the reaction mixture was heated to 140° C. over 2 hr to concentrate it. The results are shown in Table 6.

TABLE 6

| HCHO/TAAM (molar ratio) | TAAM Conversion Ratio (mole %) | Yield of N-methyl-TAAM (mole %) | Selectivity for N-methyl-TAAM (mole %) |
| --- | --- | --- | --- |
| 2.3 | 99.8 | 97.6 | 97.8 |
| 2.6 | 99.6 | 97.0 | 97.4 |

EXAMPLE 7

Eighty percent aqueous TAAM solution (TAAM: 1.0 mol) and 37% aqueous formaldehyde (HCHO: 1.0 mol) were placed in a reactor provided with a packed column (10×1 cmφ), and the mixture was dissolved by heating at 70° C. Then, the mixture was heated to 98° C. (reflux temperature) and 37% aqueous formaldehyde (HCHO: 1.3 mol) was fed over 1 hr. Thereafter, the reaction mixture was reacted under atmospheric pressure for another 2 hr. Subsequently, the reaction mixture was heated to 140° C. over 1 hr to concentrate it. The yield of N-methyl-TAAM was 99 mole %.

REFERENCE EXAMPLE 1

Eighty percent aqueous TAAM solution, 37% aqueous formaldehyde and formic acid were placed in a reactor to give a molar ratio of TAAM:HCHO:HCOOH=1:2:1. The mixture was reacted at 100° C. under atmospheric pressure for 8 hr.

As a result, TAAM conversion was 99 mole %, N-methyl-TAAM selectivity 99 mole %, and N-methyl-TAAM yield 98 mole %.

What is claimed is:

1. A method for preparing 4-hydroxy-1,2,2,6,6-pentamethylpiperidine comprising the following steps:

(i) reacting 4-hydroxy-2,2,6,6-tetramethylpiperidine with at least one compound selected from the group consisting of formaldehyde, paraformaldehyde and trioxane, optionally in the presence of formic acid;

(ii) neutralizing the reaction product of step (i) by adding a base thereto; and (iii) after the neutralization, separating the crude product from the aqueous layer and crystallizing and filtering the crude product;

wherein a water content of the crystals of 4-hydroxy-1,2,2,6,6-pentamethylpiperidine obtained in step (iii) is controlled to be 3% by weight or less by regulating a base concentration of the aqueous layer obtained after the neutralization to be 25% by weight or more.

2. The method according to claim 1, wherein the crystals of 4-hydroxy-1,2,2,6,6-pentamethylpiperidine with a water content of 3% by weight or less that are obtained in step (iii) are dried.

3. The method according to claim 1, wherein the reaction product is concentrated before it is neutralized.

4. The method according to claim 1 or 3, wherein a water-immiscible organic solvent is added to the reaction product or a concentrated reaction product before neutralization thereof.

5. The method according to claim 1, wherein a base with a concentration of 30% by weight or more is added in the neutralization step.

6. The method according to claim 1, wherein the base used for the neutralization is sodium hydroxide.

7. The method according to claim 1, wherein the aqueous layer from which the crude product has been separated after the neutralization is recycled to the neutralization step (ii).

8. The method according to claim 5, wherein the organic solvent is the mother liquor resulting from the crystallization conducted in step (iii).

9. The method according to claim 1, wherein the formic acid is added in an amount ranging from zero to less than that of 4-hydroxy-2,2,6,6-tetramethylpiperidine in terms of moles.

* * * * *